United States Patent
Astier et al.

(10) Patent No.: US 9,168,717 B2
(45) Date of Patent: Oct. 27, 2015

(54) SOLID STATE NANOPORE DEVICES FOR NANOPORE APPLICATIONS TO IMPROVE THE NANOPORE SENSITIVITY AND METHODS OF MANUFACTURE

(71) Applicant: INTERNATIONAL BUSINESS MACHINES CORPORATION, Armonk, NY (US)

(72) Inventors: Yann Astier, White Plains, NY (US); Jingwei Bai, Elmsford, NY (US); Satyavolu Papa Rao, Poughkeepsie, NY (US); Kathleen Reuter, Yorktown Heights, NY (US); Joshua T. Smith, Croton on Hudson, NY (US)

(73) Assignee: GLOBALFOUNDRIES U.S. 2 LLC, Hopewell Junction, NY (US)

( * ) Notice: Subject to any disclaimer, the term of this patent is extended or adjusted under 35 U.S.C. 154(b) by 128 days.

(21) Appl. No.: 14/024,165

(22) Filed: Sep. 11, 2013

(65) Prior Publication Data
US 2015/0056407 A1    Feb. 26, 2015

Related U.S. Application Data

(63) Continuation of application No. 14/010,158, filed on Aug. 26, 2013, now Pat. No. 9,085,120.

(51) Int. Cl.
*B32B 3/24* (2006.01)
*B81B 1/00* (2006.01)
(Continued)

(52) U.S. Cl.
CPC ............. *B32B 3/266* (2013.01); *B81B 1/004* (2013.01); *G01N 27/4145* (2013.01); *G01N 27/4146* (2013.01); *G01N 33/48721* (2013.01); *B32B 2250/03* (2013.01); *B32B 2307/204* (2013.01); *B32B 2457/00* (2013.01); *B81B 2201/0214* (2013.01); *B81B 2203/0127* (2013.01); *B81B 2203/0353* (2013.01)

(58) Field of Classification Search
None
See application file for complete search history.

(56) References Cited

U.S. PATENT DOCUMENTS

| 4,919,810 A | 4/1990 | Itoh et al. |
| 5,270,125 A * | 12/1993 | America et al. ............. 428/698 |

(Continued)

FOREIGN PATENT DOCUMENTS

WO    WO 00/78668 A1 * 12/2000 ................ B81B 1/00

OTHER PUBLICATIONS

Chang et al., Fabrication and characterization of solid-state nanopores using a field emission scanning electron microscope, Apr. 2006, Birck and NCN Publications, Paper 4.*

(Continued)

*Primary Examiner* — Jeff Vonch
(74) *Attorney, Agent, or Firm* — Andrew M. Calderon; Roberts Mlotkowski Safran & Cole, P.C.

(57) ABSTRACT

Solid state nanopore devices for nanopore applications and methods of manufacture are disclosed herein. The method includes forming a membrane layer on an underlying substrate. The method further includes forming a hole in the membrane layer. The method further comprises plugging the hole with a sacrificial material. The method further includes forming a membrane over the sacrificial material. The method further includes removing the sacrificial material within the hole and portions of the underlying substrate. The method further includes drilling an opening in the membrane, aligned with the hole.

3 Claims, 5 Drawing Sheets

(51) Int. Cl.
- *B82Y 99/00* (2011.01)
- *B32B 3/26* (2006.01)
- *G01N 27/414* (2006.01)
- *G01N 33/487* (2006.01)
- *B82Y 5/00* (2011.01)
- *B82Y 15/00* (2011.01)
- *B82Y 40/00* (2011.01)

(56) References Cited

U.S. PATENT DOCUMENTS

| | | | |
|---|---|---|---|
| 5,919,364 A * | 7/1999 | Lebouitz et al. | 210/321.84 |
| 6,412,928 B1 | 7/2002 | Anagnostopoulos et al. | |
| 7,717,271 B2 | 5/2010 | Ramaswamy et al. | |
| 7,824,548 B2 | 11/2010 | DiLeo et al. | |
| 8,137,442 B2 | 3/2012 | Pintault et al. | |
| 8,182,590 B2 | 5/2012 | Striemer et al. | |
| 8,307,992 B2 | 11/2012 | Noda et al. | |
| 2002/0170875 A1* | 11/2002 | Benzel et al. | 216/2 |
| 2003/0205552 A1* | 11/2003 | Hansford et al. | 216/2 |
| 2004/0149688 A1* | 8/2004 | Fuchs et al. | 216/56 |
| 2005/0014162 A1* | 1/2005 | Barth et al. | 435/6 |
| 2005/0068608 A1 | 3/2005 | Campbell et al. | |
| 2005/0069687 A1* | 3/2005 | Barth | 428/216 |
| 2005/0102721 A1* | 5/2005 | Barth | 977/DIG. 001 |
| 2007/0020146 A1* | 1/2007 | Young et al. | 422/82.01 |
| 2007/0284682 A1 | 12/2007 | Laming et al. | |
| 2008/0311375 A1* | 12/2008 | Harnack et al. | 428/315.7 |
| 2009/0162989 A1 | 6/2009 | Cho et al. | |
| 2010/0038734 A1* | 2/2010 | Kasai et al. | 257/416 |
| 2011/0120868 A1* | 5/2011 | Lindsay et al. | 204/452 |
| 2011/0223652 A1* | 9/2011 | Peng et al. | 435/287.2 |
| 2011/0316100 A1 | 12/2011 | Kim et al. | |
| 2012/0013989 A1 | 1/2012 | Choi et al. | |
| 2012/0021204 A1* | 1/2012 | Pei et al. | 428/314.2 |
| 2012/0040512 A1* | 2/2012 | Li et al. | 438/478 |
| 2012/0103821 A1* | 5/2012 | Harrer et al. | 205/84 |
| 2012/0118730 A1* | 5/2012 | Liang et al. | 204/269 |
| 2012/0267729 A1* | 10/2012 | Dang et al. | 257/414 |
| 2013/0037410 A1* | 2/2013 | Xu et al. | 204/601 |
| 2013/0092541 A1* | 4/2013 | Drndic et al. | 204/543 |
| 2013/0299945 A1* | 11/2013 | Stolovitzky et al. | 257/618 |
| 2013/0334048 A1* | 12/2013 | Balagurusamy, Venkat K. | 204/518 |
| 2014/0062454 A1* | 3/2014 | Jeon et al. | 324/71.1 |
| 2014/0262820 A1* | 9/2014 | Kuan et al. | 205/665 |

OTHER PUBLICATIONS

Chen et al., Microfabrication of nanopore devices without nanolithography, Jan. 2008, Micro Electro Mechanical Systems IEEE 21st International Conference.*

DileepNanotech, Fabrication of solid-state nanopores (d < 10 nm), Oct. 2011.*

Uddin et al., Integration of solid-state nanopores in a 0.5 μm cmos foundry process, Mar. 2013, Nanotechnology, 24(15).*

Office Action for related U.S. Appl. No. 14/010,158 dated Dec. 10, 2014, 16 pages.

Notice of Allowance for related U.S. Appl. No. 14/010,158 dated Apr. 13, 2015, 10 pages.

* cited by examiner

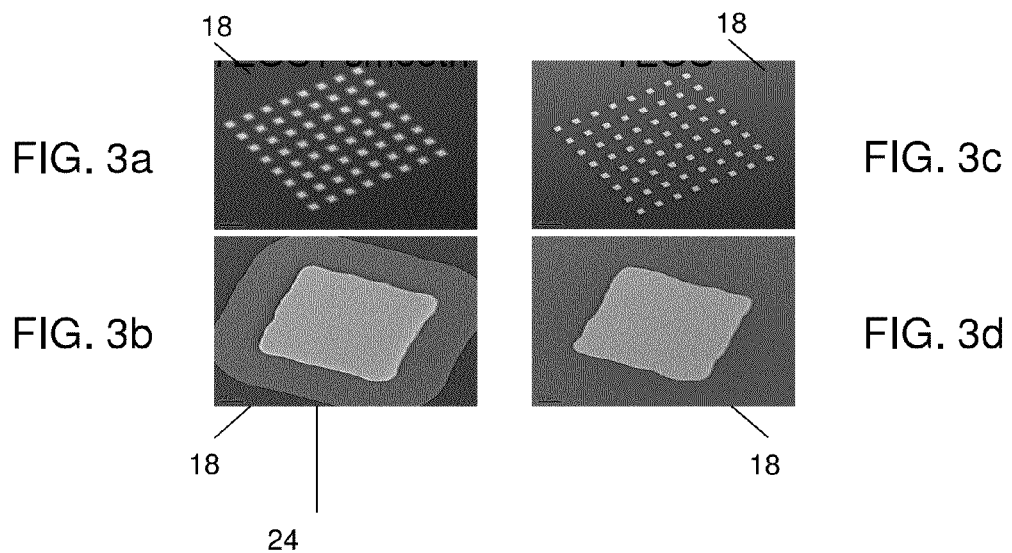
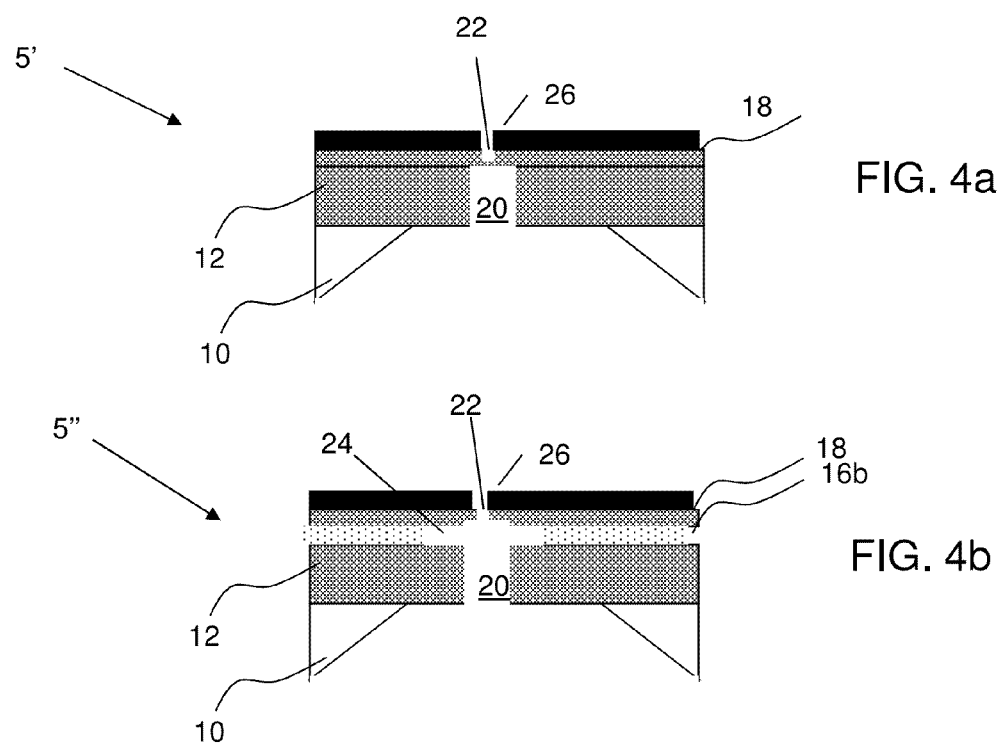

SOLID STATE NANOPORE DEVICES FOR NANOPORE APPLICATIONS TO IMPROVE THE NANOPORE SENSITIVITY AND METHODS OF MANUFACTURE

FIELD OF THE INVENTION

The invention relates to solid state nanopore devices and methods of manufacture and, more particularly, to solid state nanopore devices for nanopore applications and methods of manufacture.

BACKGROUND

Solid state nanopore devices have been demonstrated for many potential applications in bio-sensing and other applications. For example, single molecular detection of DNA, RNA, and protein molecules has been realized in solid state nanopore devices. Also, bio-molecule binding affinity has been studied using solid state nanopore devices.

An important factor to improve the nanopore sensitivity to molecular translocation is to reduce the membrane thickness. A major challenge is that the thin membrane, especially when the membrane thickness is in the sub-10 nm regime, is mechanically fragile while suspending over a micron or tens of micron window size. The techniques typically used to generate thin membrane structures at these extremely-scaled sizes, such as reactive ion etch or ion milling to locally thin down a relative thicker membrane, are incapable to incorporate more functional structures on the top of the membrane such as field effect transistors (FETs) or tunneling junction electrodes.

Accordingly, there exists a need in the art to overcome the deficiencies and limitations described hereinabove.

SUMMARY

In a first aspect of the invention, a method comprises forming a membrane layer on an underlying substrate. The method further comprises forming a hole in the membrane layer. The method further comprises plugging the hole with a sacrificial material. The method further comprises forming a membrane over the sacrificial material. The method further comprises removing the sacrificial material within the hole. The method further comprises drilling an opening in the membrane, aligned with the hole.

In another aspect of the invention, a method comprises forming a dielectric layer on an underlying substrate. The method further comprises forming a hole in the dielectric layer by lithography and etching processes. The method further comprises plugging the hole with a sacrificial material to form a sacrificial plug. The plugging comprises blanket depositing of an oxide material to a thickness greater than the depth of the hole, and planarizing the oxide material to the surface of the dielectric layer. The method further comprises forming a membrane over the sacrificial plug. The method further comprises removing the sacrificial plug and portions of the underlying substrate. The method further comprises drilling an opening in the membrane, aligned with the hole.

In yet another aspect of the invention, a structure comprises: a dielectric layer on an underlying substrate; a hole in the dielectric layer and underlying substrate; and a membrane over the sacrificial plug having an opening suspended and aligned with the hole.

In another aspect of the invention, a design structure tangibly embodied in a machine readable storage medium for designing, manufacturing, or testing an integrated circuit is provided. The design structure comprises the structures of the present invention. In further embodiments, a hardware description language (HDL) design structure encoded on a machine-readable data storage medium comprises elements that when processed in a computer-aided design system generates a machine-executable representation of the ultrathin membranes for nanopore applications, which comprises the structures of the present invention. In still further embodiments, a method in a computer-aided design system is provided for generating a functional design model of the ultrathin membranes for nanopore applications. The method comprises generating a functional representation of the structural elements of the ultrathin membranes for nanopore applications.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

FIGS. 3a-3d show structures in accordance with aspects of the present invention;

FIGS. 4a and 4b show bio-sensing structures in accordance with aspects of the present invention.

DETAILED DESCRIPTION

The invention relates to solid state nanopore devices and methods of manufacture and, more particularly, to solid state nanopore devices for nanopore applications and methods of manufacture. In more specific embodiments, the present invention is directed to methods of creating an ultra thin membrane suspended over a few hundred nanometer window supported by a thicker membrane which can span over a micron or tens of microns wide window on a Si wafer. In embodiments, this is achieved by forming a thin membrane film on top of a planarized thick membrane film with a sacrificial plug. After removal of the sacrificial plug, a small sized opening can be formed in the membrane file, aligned with the hole formed by the removal of the sacrificial plug.

Advantageously, fabrication flows of the present invention allow a thin membrane to span only over a small area, which makes it mechanically strong enough to undergo post process and test procedures. Additionally, the thickness of the membrane is dependent on a formation method (e.g., growth or deposition process), which is better controlled than etching methods currently used to form thin membranes. Moreover, the fabricated membrane of the present invention has a flat top surface, making it compatible with additional functional structures such as FET or tunneling junction electrodes.

Figure 1A:
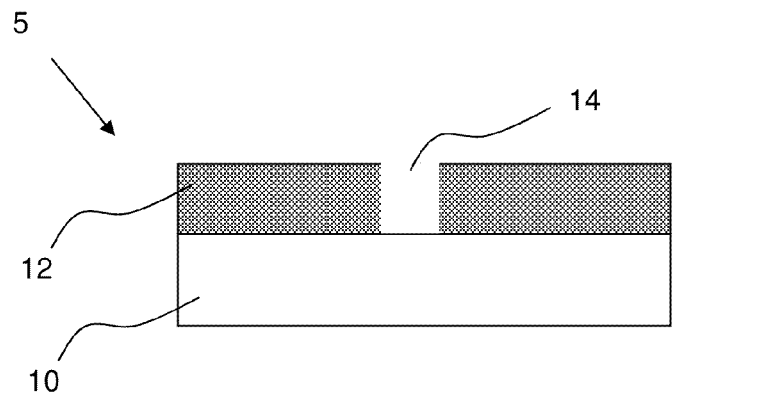
FIGS. 1a-1f show processes and respective structures in accordance with aspects of the present invention.

FIG. 1a shows a beginning structure and respective processing steps in accordance with aspects of the present invention. In particular, the structure 5 of FIG. 1 includes a substrate 10. The substrate 10 can be, for example, a Si wafer; although other materials are contemplated by the present invention. A thick membrane 12, e.g., dielectric layer, is deposited on the substrate 10. In embodiments, the dielectric layer 12 can be, for example, SiNx, with thickness of about 20 nm to 500 nm. The dielectric layer 12 can be deposited using any conventionally known deposition method, such as, for example, low-pressure chemical vapor deposition (LPCVD).

In embodiments, a hole 14 is formed within the dielectric layer 12. In embodiments, the hole 14 can be formed using standard lithography and etching processes. For example, a resist can be applied to the dielectric layer 12, which is patterned by local exposure to an energy source (e.g., an electron beam). A reactive ion etch (RIE) is performed through the patterned resist to form the hole 14 within the dielectric layer 12 while masking the rest of the dielectric layer 12. The resist can then be stripped or removed using conventional descum or stripping processes, such as oxygen plasma ashing. In embodiments, the hole can be about 200 nm or less in size; although other dimensions are also contemplated by the present invention. In embodiments, the hole can be any desired shape.

Figure 1B:
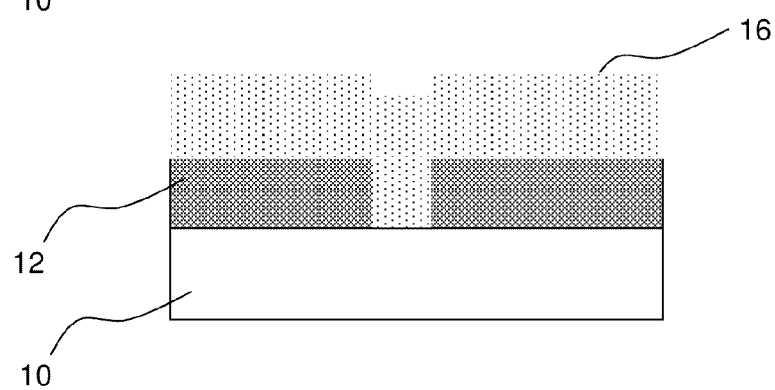

In FIG. 1b, the hole 14 is filled with a sacrificial material 16. In embodiments, the sacrificial material 16 can be, for example, $SiO_2$, formed by a blanket CVD process or other conventional processes, e.g., plasma enhanced CVD (PECVD) or atomic layer deposition (ALD). In embodiments, the thickness of the sacrificial material 16 should be thicker than the depth of the hole 14.

Figure 1C:
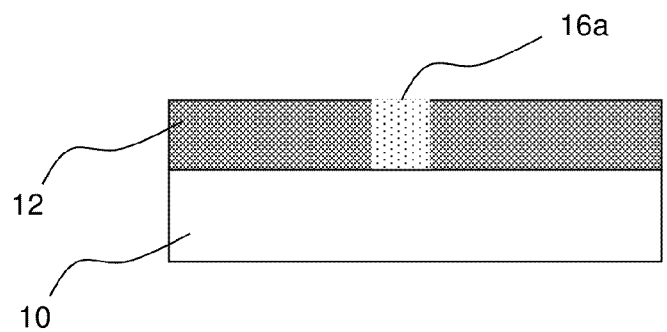

In FIG. 1c, the sacrificial material 16 undergoes a planarization process. For example, the sacrificial material 16 can be planarized using a chemical mechanical planarization (CMP) process to planarize the sacrificial material 16 to the surface of the dielectric layer 12. In this way, the sacrificial material 16 will plug the hole 14, resulting in a sacrificial plug 16a. In embodiments, the CMP process should not cause any significant dishing in the sacrificial plug 16a, depending on the size of the original hole 14.

Figure 1D:
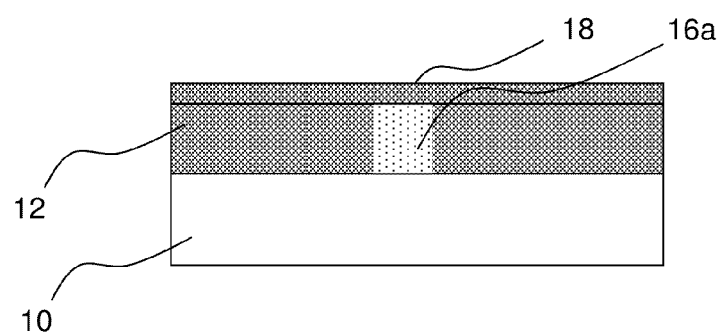

In FIG. 1d, an arbitrary thickness of membrane material 18 is deposited on top of the planarized substrate, e.g., sacrificial plug 16a and dielectric layer 12. In this case, the membrane thickness 18 can be as thin as a few nanometers, depending on the size of the sacrificial plug 16a. In embodiments, the membrane material 18 can be, for example, SiNx, with thickness of about 10 nm. The membrane material 18 can be blanket deposited using any conventionally known deposition method, e.g., LPCVD.

Figure 1E:
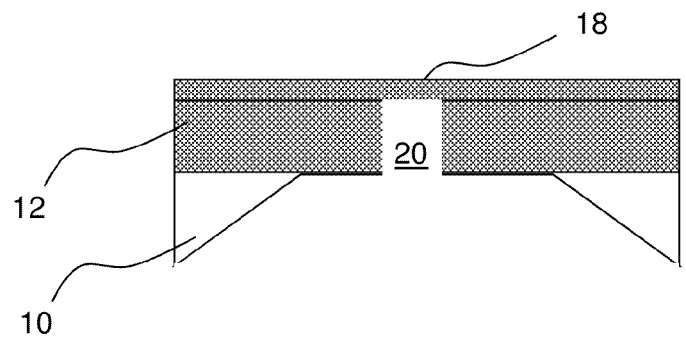

As shown in FIG. 1e, the sacrificial plug 16a and portions of the underlying substrate 10 are removed using conventional etching techniques, such as RIE or wet etch processes. In embodiments, the underlying substrate 10 and sacrificial plug 16a can be removed using different etching steps, each of which is selective to the material being etched, e.g., Si material and oxide material. For example, oxide material can be etched using an $HF_2$ dip or dilute buffered oxide etch (BOE) process. In embodiments, the removal of the sacrificial plug area will result in a hole 20.

Figure 1F:
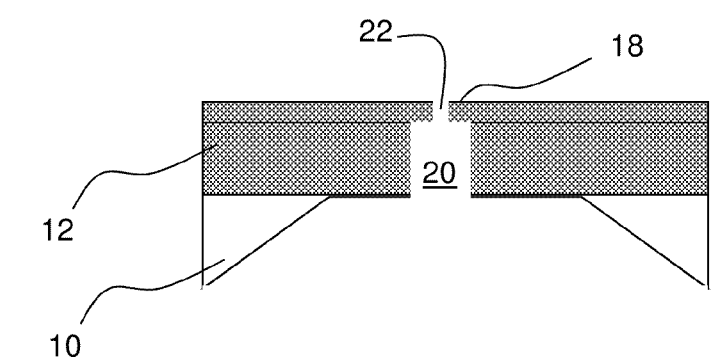

In FIG. 1f, the membrane material 18 undergoes a drilling process to open a hole (opening) 22 in the membrane material 18. In embodiments, the opening 22 is aligned with the hole 20 (resulting from the removal of the oxide material). More specifically, the opening 22 is suspended over the hole 20, formed in the dielectric layer 12. The opening 22 can be from 1 nm to about 30 nm in diameter. Functional electrodes with a very narrow gap may be used as a mask to achieve the smaller hole sizes of 1 nm to 5 nm. The opening 22 can be formed by a transmission electron microscopy (TEM) process or focused ion beam (FIB) process, from either the front side or back side of the structure (although formation from the back side is preferred). As should be understood by those of ordinary skill in the art, the TEM process is a microscopy technique whereby a beam of electrons is transmitted through a thin specimen, e.g., membrane material 18. The opening 22 can be drilled by either process within seconds of beam focus.

FIGS. 2a-2d show processes and respective structures in accordance with additional aspects of the present invention. More specifically, starting from the structure of FIG. 1c, an option sacrificial material 16b is formed over the planarized substrate, e.g., sacrificial plug 16a and dielectric layer 12. In this case, the option sacrificial material 16b can have a thickness of about a few nanometers. In embodiments, the option sacrificial material 16b can be, for example, $SiO_2$ or other dielectric material, and is preferably the same material as used for the sacrificial plug 16a. In embodiments, the option sacrificial material 16b can be grown and, if necessary, planarized using CMP processes. The option sacrificial material 16b can be used to minimize edge erosion and possible dishing effect which may occurs to the sacrificial plug 16a, thereby enabling a flatter surface to be achieved, such as might be necessary for the inclusion of thin function electrodes, for example.

Figure 2A:
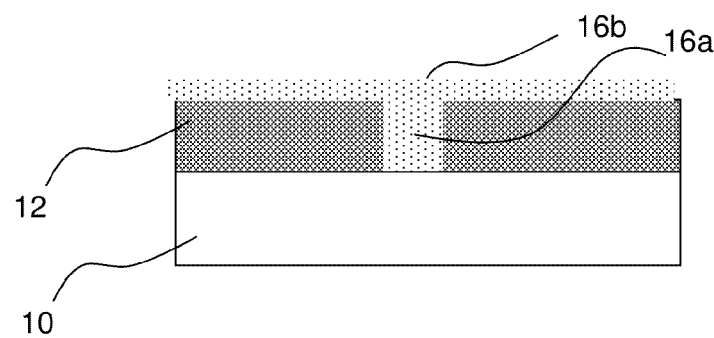
FIGS. 2a-2d show processes and respective structures in accordance with additional aspects of the present invention.
Figure 2B:
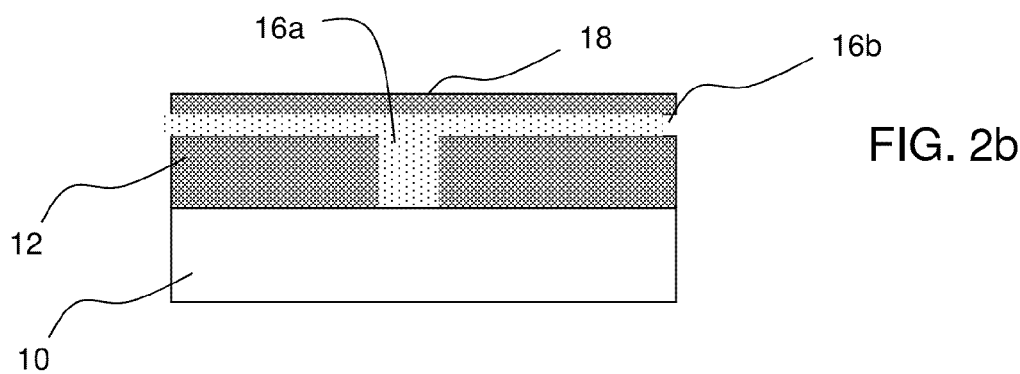

In FIG. 2b, an arbitrary thickness of membrane material 18 is deposited on top of the planarized substrate, e.g., option sacrificial material 16b. In this case, the membrane thickness 18 can be as thin as a few nanometers. In embodiments, the membrane material 18 can be, for example, SiNx, with thickness of about 10 nm. The membrane material 18 can be blanket deposited using any conventionally known deposition method, e.g., LPCVD.

Figure 2C:
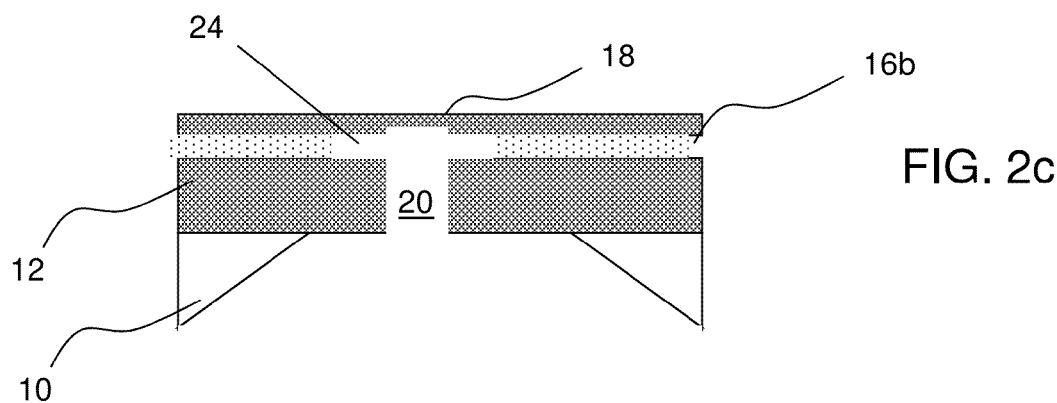

As shown in FIG. 2c, the sacrificial plug 16a and portions of the underlying substrate 10 are removed using conventional etching techniques. In embodiments, the underlying substrate 10 and sacrificial plug area 16a can be removed using different etching steps, each of which is selective to the material being etched, e.g., Si material and oxide material. For example, oxide material can be etched using an $HF_2$ dip or dilute (BOE). In embodiments, the removal of the sacrificial plug 16a will result in a hole 20 and undercut (air gap) formation 24 between the membrane material 18 and the dielectric layer 12.

Figure 2D:
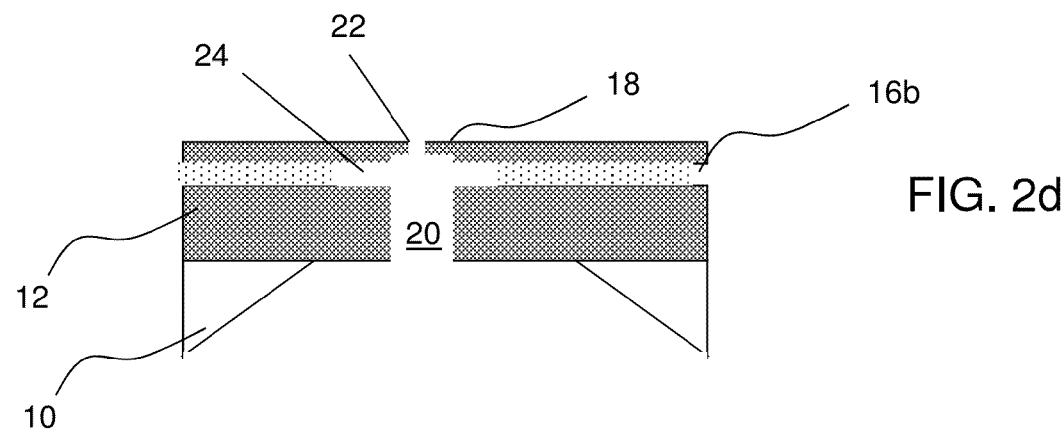

In FIG. 2d, the membrane material 18 undergoes a drilling process to open a hole (opening) 22 in the membrane material 18. In embodiments, the opening 22 is aligned with the hole 20 (resulting from the removal of the oxide material), and can be about 1 nm to about 30 nm in diameter. Functional electrodes with a very narrow gap may be used as a mask to achieve the smaller hole sizes of 1 nm to 5 nm. As in the previous aspect of the present invention, the opening 22 is suspended over the hole 20, and is formed by a transmission electron microscopy (TEM) process or focused ion beam (FIB) process, from either the front side or back side of the structure (although formation from the back side is preferred).

FIGS. 3a-3d show various views of the structures fabricated in the processes described above. More specifically, FIGS. 3a and 3b show structures fabricated in accordance with the processes described with regard to FIGS. 2a-2d; whereas, FIGS. 3c and 3d show structures fabricated in accordance with the processes described with regard to FIGS. 1a-1f. In the embodiments shown in FIGS. 3a-3d, the dielectric material (dielectric material 12) is SiNx, deposited to a thickness of about 50 nm with a locally patterned hole array (holes 14), each having a width of about 200 nm. The holes are filled with TEOS oxide and then polished down. The membrane 18, e.g., nitride film, is deposited to a thickness of about 10 nm. FIG. 3b shows the undercut 24; whereas, FIG. 3d is devoid of the undercut (due to the fact that a second oxide layer (e.g., layer 16b) is not used in the fabrication process).

FIG. 4a shows a structure starting from the structure of FIG. 1f; whereas, FIG. 4b shows a structure starting from the structure of FIG. 2d. In particular, FIGS. 4a and 4b show a structure 5' and 5", respectively, with electrodes 26 positioned on both sides of the opening 22. In embodiments, the electrodes 26 can be fabricated using any conventional metal deposition and patterning processes. For example, metal or metal alloy material, e.g., palladium, gold, or other metal, can be deposited using an electron-beam, sputter, or thermal deposition process. The metal can then be patterned by conventional RIE processes, known to those of skill in the art, to form the electrodes 26. In embodiments, the electrodes 26 can be representative of a FET or tunneling junction electrodes.

Figure 5:
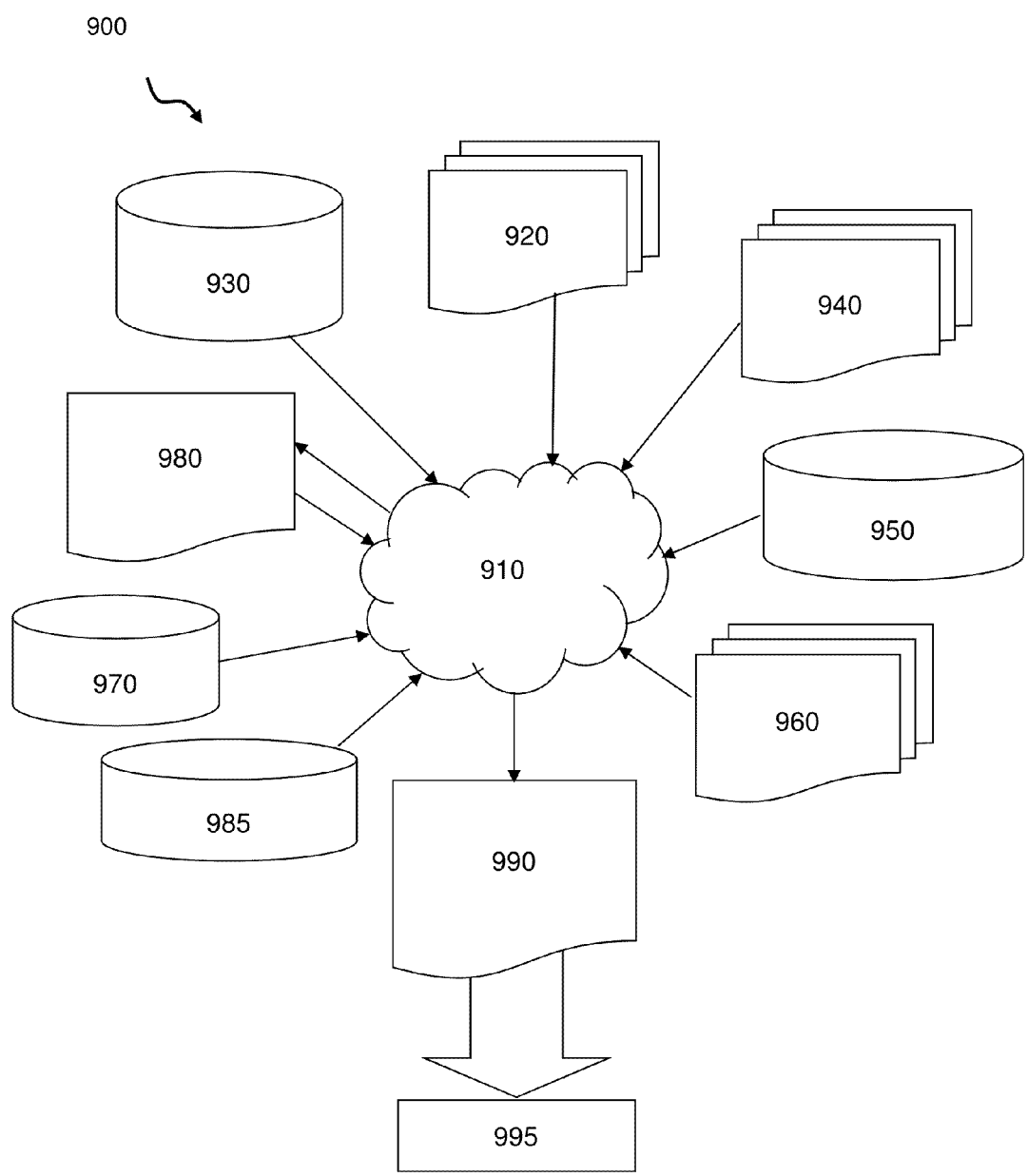
FIG. 5 is a flow diagram of a design process used in semiconductor design, manufacture, and/or test.

FIG. 5 is a flow diagram of a design process used in semiconductor design, manufacture, and/or test. FIG. 5 shows a block diagram of an exemplary design flow 900 used for example, in semiconductor IC logic design, simulation, test, layout, and manufacture. Design flow 900 includes processes, machines and/or mechanisms for processing design structures or devices to generate logically or otherwise functionally equivalent representations of the design structures and/or devices described above and shown in FIGS. 1a-1f, 2a-2d, 3a-3d, 4a and 4b. The design structures processed and/or generated by design flow 900 may be encoded on machine-readable transmission or storage media to include data and/or instructions that when executed or otherwise processed on a data processing system generate a logically, structurally, mechanically, or otherwise functionally equivalent representation of hardware components, circuits, devices, or systems. Machines include, but are not limited to, any machine used in an IC design process, such as designing, manufacturing, or simulating a circuit, component, device, or system. For example, machines may include: lithography machines, machines and/or equipment for generating masks (e.g. e-beam writers), computers or equipment for simulating design structures, any apparatus used in the manufacturing or test process, or any machines for programming functionally equivalent representations of the design structures into any medium (e.g. a machine for programming a programmable gate array).

Design flow 900 may vary depending on the type of representation being designed. For example, a design flow 900 for building an application specific IC (ASIC) may differ from a design flow 900 for designing a standard component or from a design flow 900 for instantiating the design into a programmable array, for example a programmable gate array (PGA) or a field programmable gate array (FPGA) offered by Altera® Inc. or Xilinx® Inc.

FIG. 5 illustrates multiple such design structures including an input design structure 920 that is preferably processed by a design process 910. Design structure 920 may be a logical simulation design structure generated and processed by design process 910 to produce a logically equivalent functional representation of a hardware device. Design structure 920 may also or alternatively comprise data and/or program instructions that when processed by design process 910, generate a functional representation of the physical structure of a hardware device. Whether representing functional and/or structural design features, design structure 920 may be generated using electronic computer-aided design (ECAD) such as implemented by a core developer/designer. When encoded on a machine-readable data transmission, gate array, or storage medium, design structure 920 may be accessed and processed by one or more hardware and/or software modules within design process 910 to simulate or otherwise functionally represent an electronic component, circuit, electronic or logic module, apparatus, device, or system such as those shown in FIGS. 1a-1f, 2a-2d, 3a-3d, 4a and 4b. As such, design structure 920 may comprise files or other data structures including human and/or machine-readable source code, compiled structures, and computer-executable code structures that when processed by a design or simulation data processing system, functionally simulate or otherwise represent circuits or other levels of hardware logic design. Such data structures may include hardware-description language (HDL) design entities or other data structures conforming to and/or compatible with lower-level HDL design languages such as Verilog and VHDL, and/or higher level design languages such as C or C++.

Design process 910 preferably employs and incorporates hardware and/or software modules for synthesizing, translating, or otherwise processing a design/simulation functional equivalent of the components, circuits, devices, or logic structures shown in FIGS. 1a-1f, 2a-2d, 3a-3d, 4a and 4b to generate a netlist 980 which may contain design structures such as design structure 920. Netlist 980 may comprise, for example, compiled or otherwise processed data structures representing a list of wires, discrete components, logic gates, control circuits, I/O devices, models, etc. that describes the connections to other elements and circuits in an integrated circuit design. Netlist 980 may be synthesized using an iterative process in which netlist 980 is resynthesized one or more times depending on design specifications and parameters for the device. As with other design structure types described herein, netlist 980 may be recorded on a machine-readable data storage medium or programmed into a programmable gate array. The medium may be a non-volatile storage medium such as a magnetic or optical disk drive, a programmable gate array, a compact flash, or other flash memory. Additionally, or in the alternative, the medium may be a system or cache memory, buffer space, or electrically or optically conductive devices and materials on which data packets may be transmitted and intermediately stored via the Internet, or other networking suitable means.

Design process 910 may include hardware and software modules for processing a variety of input data structure types including netlist 980. Such data structure types may reside, for example, within library elements 930 and include a set of commonly used elements, circuits, and devices, including models, layouts, and symbolic representations, for a given manufacturing technology (e.g., different technology nodes, 32 nm, 45 nm, 90 nm, etc.). The data structure types may further include design specifications 940, characterization data 950, verification data 960, design rules 970, and test data files 985 which may include input test patterns, output test results, and other testing information. Design process 910 may further include, for example, standard mechanical design processes such as stress analysis, thermal analysis, mechanical event simulation, process simulation for operations such as casting, molding, and die press forming, etc. One of ordinary skill in the art of mechanical design can appreciate the extent of possible mechanical design tools and applications used in design process 910 without deviating from the scope and spirit of the invention. Design process 910 may also include modules for performing standard circuit design processes such as timing analysis, verification, design rule checking, place and route operations, etc.

Design process 910 employs and incorporates logic and physical design tools such as HDL compilers and simulation model build tools to process design structure 920 together with some or all of the depicted supporting data structures along with any additional mechanical design or data (if applicable), to generate a second design structure 990.

Design structure 990 resides on a storage medium or programmable gate array in a data format used for the exchange of data of mechanical devices and structures (e.g. information stored in a IGES, DXF, Parasolid XT, JT, DRG, or any other suitable format for storing or rendering such mechanical design structures). Similar to design structure 920, design structure 990 preferably comprises one or more files, data structures, or other computer-encoded data or instructions that reside on transmission or data storage media and that when processed by an ECAD system generate a logically or otherwise functionally equivalent form of one or more of the embodiments of the invention shown in FIGS. 1a-1f, 2a-2d, 3a-3d, 4a and 4b. In one embodiment, design structure 990 may comprise a compiled, executable HDL simulation model that functionally simulates the devices shown in FIGS. 1a-1f, 2a-2d, 3a-3d, 4a and 4b.

Design structure 990 may also employ a data format used for the exchange of layout data of integrated circuits and/or symbolic data format (e.g. information stored in a GDSII (GDS2), GL1, OASIS, map files, or any other suitable format for storing such design data structures). Design structure 990 may comprise information such as, for example, symbolic data, map files, test data files, design content files, manufacturing data, layout parameters, wires, levels of metal, vias, shapes, data for routing through the manufacturing line, and any other data required by a manufacturer or other designer/developer to produce a device or structure as described above and shown in FIGS. 1a-1f, 2a-2d, 3a-3d, 4a and 4b. Design structure 990 may then proceed to a stage 995 where, for example, design structure 990: proceeds to tape-out, is released to manufacturing, is released to a mask house, is sent to another design house, is sent back to the customer, etc.

The method as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A nanopore structure, comprising:
    a dielectric layer on an underlying substrate;
    a first hole in the underlying substrate;
    a second hole in the dielectric layer;
    a membrane over the dielectric layer, the membrane having an opening suspended and aligned with the hole; and
    an air gap, between the membrane and the dielectric layer wherein:
        the opening has a smaller diameter than the second hole;
        the second hole has a smaller diameter than the air gap;
        the air gap has a smaller diameter than the first hole; and
    an oxide material between the dielectric layer and the membrane, the oxide material containing the air gap.

2. The structure of claim 1, further comprising a functional electrode used as a mask to achieve a hole diameter of 1 nm to 5 nm.

3. The structure of claim 1, further comprising an electrode formed above the membrane, wherein the electrode is positioned on both sides of the opening and the opening has a constant width.

* * * * *